US009339803B2

(12) United States Patent
Wickramasinghe et al.

(10) Patent No.: US 9,339,803 B2
(45) Date of Patent: May 17, 2016

(54) CATALYTIC MEMBRANES AND APPLICATIONS THEREOF

(71) Applicant: The Board of Trustees of the University of Arkansas, Little Rock, AR (US)

(72) Inventors: Sumith Ranil Wickramasinghe, Fayetteville, AR (US); Xianghong Qian, Fayetteville, AR (US); Mathias Ulbricht, Berlin (DE); Qian Yang, Essen (DE)

(73) Assignees: Board of Trustees of the University of Arkansas, Little Rock, AR (US); Universitat Duisburg-Essen, Essen (DE)

( * ) Notice: Subject to any disclaimer, the term of this patent is extended or adjusted under 35 U.S.C. 154(b) by 0 days.

(21) Appl. No.: 14/355,364

(22) PCT Filed: Oct. 31, 2012

(86) PCT No.: PCT/US2012/062690
§ 371 (c)(1),
(2) Date: Apr. 30, 2014

(87) PCT Pub. No.: WO2013/066941
PCT Pub. Date: May 10, 2013

(65) Prior Publication Data

US 2014/0371340 A1 Dec. 18, 2014

Related U.S. Application Data

(60) Provisional application No. 61/553,547, filed on Oct. 31, 2011.

(51) Int. Cl.
*B01D 71/06* (2006.01)
*B01J 31/06* (2006.01)

(Continued)

(52) U.S. Cl.
CPC ............ *B01J 31/06* (2013.01); *B01D 67/0093* (2013.01); *B01D 71/70* (2013.01); *B01J 8/009* (2013.01); *B01J 19/2475* (2013.01);
(Continued)

(58) Field of Classification Search
CPC .................................................. C08J 2339/04
See application file for complete search history.

(56) References Cited

U.S. PATENT DOCUMENTS

2007/0166590 A1* 7/2007 Nakano et al. .................. 429/33
2013/0032530 A1* 2/2013 Minehara et al. ........ 210/500.28

FOREIGN PATENT DOCUMENTS

EP 2 033 974 A1 3/2009
WO WO 2011122560 A1 * 10/2011

OTHER PUBLICATIONS

Evans, D. A. and Ripin, D. H. pKa's of of Acids. http://evans.harvard.edu/pdf/evans_pKa_table.pdf. As viewed on Jul. 27, 2015.*

(Continued)

*Primary Examiner* — Robert C Boyle
*Assistant Examiner* — Stephen Rieth
(74) *Attorney, Agent, or Firm* — Smith Moore Leatherwood LLP; J. Clinton Wimbish

(57) ABSTRACT

In one aspect, catalytic membranes are described herein. In some embodiments, a catalytic membrane comprises a surface functionalized with a polymer, the polymer comprising cellulose solubilization functionalities and acid functionalities for the catalytic hydrolysis of cellulose and/or hemicellulose.

9 Claims, 5 Drawing Sheets

(51) Int. Cl.

| | |
|---|---|
| ***B01D 71/70*** | (2006.01) |
| ***B01J 31/02*** | (2006.01) |
| ***B01J 31/10*** | (2006.01) |
| ***B01D 67/00*** | (2006.01) |
| ***C13B 20/16*** | (2011.01) |
| ***C13K 13/00*** | (2006.01) |
| ***C12M 1/00*** | (2006.01) |
| ***B01J 19/24*** | (2006.01) |
| ***B01J 8/00*** | (2006.01) |
| *C13K 1/02* | (2006.01) |

(52) U.S. Cl.

CPC ......... *B01J 31/0225* (2013.01); *B01J 31/0284* (2013.01); *B01J 31/0285* (2013.01); *B01J 31/0295* (2013.01); *B01J 31/069* (2013.01); *B01J 31/10* (2013.01); *C12M 21/12* (2013.01); *C12M 45/06* (2013.01); *C13B 20/165* (2013.01); *C13K 13/002* (2013.01); *C13K 13/007* (2013.01); *B01D 2323/38* (2013.01); *B01J 2231/005* (2013.01); *C13K 1/02* (2013.01)

(56) References Cited

OTHER PUBLICATIONS

International Search Report and Written Opinion mailed Jan. 30, 2013 for PCT/US2012/062690, 15 pages.

Amarasekara et al., "Hydrolysis and Decomposition of Cellulose in Bronsted Acidic Ionic Liquids Under Mild Conditions," Ind. Eng. Chem. Res., vol. 48, 2009, pp. 10152-10155.

Amarasekara et al., "Synthesis of a sulfonic acid functionalized acidic ionic liquid modified silica catalyst and applications in the hydrolysis of cellulose," Catalysis Communications, Elsevier Science, vol. 11, No. 13, Jul. 26, 2010, pp. 1072-1075.

Li et al., "Acid in ionic liquid: An efficient system for hydrolysis of lignocellulose," Green Chemistry, vol. 10, 2008, pp. 177-182.

Qiao et al., "Acidic ionic liquid modified silica gel as novel solid catalysts for esterification and nitration reactions," Journal of Molecular Catalysis A: Chemical, vol. 246, 2006, pp. 65-69.

Zhang et al., "A silica gel supported dual acidic ionic liquid: an efficient and recyclable heterogeneous catalyst for the one-pot synthesis of amidoalkyl naphthols," Green Chemistry, vol. 12, 2010, pp. 2246-2254.

* cited by examiner

CATALYTIC MEMBRANES AND APPLICATIONS THEREOF

RELATED APPLICATION DATA

The present application claims priority pursuant to 35 U.S.C. §119(e) to U.S. Provisional Patent Application Ser. No. 61/553,547 filed Oct. 31, 2011, which is hereby incorporated by reference in its entirety.

FIELD

The present invention relates to catalytic membranes and, in particular, to catalytic membranes for biomass hydrolysis.

BACKGROUND

Ethanol (and other biofuels) derived from lignocellulosic materials, such as wood waste, crop stalks and grasses, is a promising renewable energy candidate to replace fossil-based fuels in a variety of applications. Because lignocellulosic materials comprise the majority of terrestrial biomass, producing ethanol from lignocellulosic material has the potential to replace up to 30% of annual petroleum consumption in the United States, while also reducing greenhouse gas emissions. In addition, the use of lignocellulosic biomass in ethanol production does not present the same food production pressures as the use of crops, such as corn.

Converting lignocellulosic biomass to ethanol can involve several steps, including chemical pretreatment of the lignocellulosic material to increase access to hydrolysable cellulose (e.g., by removing lignin), hydrolysis of cellulose to provide fermentable sugars, and fermentation of the hydrolyzed sugars. These steps can be carried out in various ways. Some methods use enzymes such as cellulases to hydrolyze cellulose. However, to achieve complete hydrolysis, a cocktail of different enzymes is typically needed. These enzymes are relatively expensive and generally cannot be reused. In addition, enzymatic hydrolysis of cellulose can be slow, sometimes requiring days or weeks to complete. Further, some methods of converting lignocellulosic biomass to ethanol involve the use of one or more hydrolytic chemical species that can be difficult to separate from desired conversion products and, in some instances, can be toxic to fermentation organisms.

SUMMARY

In one aspect, catalytic membranes operable for the hydrolysis of cellulose and/or hemicellulose are described herein. In some embodiments, a catalytic membrane comprises a surface functionalized with a polymer, the polymer comprising cellulose solubilization functionalities and acid functionalities for the catalytic hydrolysis of cellulose and/or hemicellulose. In some embodiments, the cellulose solubilization functionalities of the polymer comprise one or more imidazolium salts. The polymer, in some embodiments, is an ionic liquid.

In another aspect, a catalytic membrane described herein comprises a surface functionalized with cellulose solubilization polymer and one or more cellulose hydrolysis chemical species. Cellulose solubilization polymer comprises cellulose solubilization functionalities, such as one or more imidazolium salts. Cellulose hydrolysis chemical species comprise one or more acid functionalities for the catalytic hydrolysis of cellulose and/or hemicellulose. In some embodiments, cellulose hydrolysis chemical species comprise cellulose hydrolysis polymer comprising one or more acid functionalities for the catalytic hydrolysis of cellulose. Cellulose hydrolysis chemical species, in other embodiments, comprise non-polymeric species having one or more acid functionalities for the catalytic hydrolysis of cellulose. Further, in some embodiments, a catalytic membrane described herein comprises a surface functionalized with cellulose hydrolysis chemical species without co-functionalization with cellulose solubilization polymer.

The functionalized surface of a membrane described herein, in some embodiments, is a first side of the membrane for receiving cellulose feedstock. Moreover, in some embodiments, the membrane is porous. For example, the membrane can have a pore size sufficient to pass glucose molecules, reducing sugar molecules, oligosaccharides or mixtures thereof. The membrane, in some embodiments, has a pore size on the nanoscale suitable to pass glucose and/or other non-polysaccharide or non-oligosaccharide sugar molecules.

The membrane, in some embodiments, is non-porous. Further, the catalytic membrane comprises a second side in facing opposition to the first side. The second side, in some embodiments, is not functionalized with cellulose solubilization and/or cellulose hydrolysis species. Alternatively, the second side may be functionalized with cellulose solubilization and/or cellulose hydrolysis species.

In another aspect, membrane reactors are described herein. In some embodiments, a membrane reactor comprises a feedstock vessel, a reaction product collection vessel, and a catalytic membrane disposed between the feedstock vessel and the reaction product collection vessel. The catalytic membrane comprises a feedstock contacting surface functionalized with a polymer, the polymer comprising cellulose solubilization functionalities and acid functionalities for the catalytic hydrolysis of cellulose and/or hemicellulose. Alternatively, in some embodiments, a feedstock contacting surface of the catalytic membrane is functionalized with cellulose solubilization polymer and one or more cellulose hydrolysis chemical species. Additionally, in some embodiments, a feedstock contacting surface of the catalytic membrane can be functionalized with cellulose hydrolysis chemical species without co-functionalization with cellulose solubilization polymer.

Further, a feedstock vessel of a membrane reactor described herein can comprise a liquid phase in which lignocellulosic material is disposed. The liquid phase, in some embodiments, comprises ionic liquid, water or a mixture of ionic liquid and water.

In another aspect, methods for the hydrolysis of cellulose are described herein. In some embodiments, a method for the hydrolysis of cellulose comprises providing a cellulose feedstock and bringing the cellulose feedstock into contact with a surface of a catalytic membrane. The surface of the catalytic membrane, in some embodiments, is functionalized with a polymer comprising cellulose solubilization functionalities and acid functionalities for the catalytic hydrolysis of the cellulose. The cellulose feedstock is at least partially solubilized with the cellulose solubilization functionalities, and the solubilized cellulose feedstock is hydrolyzed with the acid functionalities to provide glucose, reducing sugars or oligosaccharides or mixtures thereof.

In other embodiments, surfaces of the membrane in contact with the cellulose feedstock are functionalized with cellulose solubilization polymer and one or more cellulose hydrolysis chemical species. The cellulose feedstock is at least partially solubilized with functionalities of the cellulose solubilization polymer, and the solubilized cellulose is hydrolyzed with acid functionalities of the hydrolysis chemical species to provide glucose, reducing sugars or oligosaccharides or mixtures thereof. Further, in some embodiments, membrane surfaces are functionalized with cellulose hydrolysis chemical species without co-functionalization with cellulose solubilization polymer.

Cellulose feedstock, in some embodiments, can be disposed in a liquid phase for interfacing with catalytic membranes described herein. A liquid phase, in some embodiments, comprises water, ionic liquid or a mixture of water and ionic liquid. In some embodiments, the presence of ionic liquid alone or in a mixture with water can assist in solubilizing lignocellulosic material in preparation for the hydrolysis of cellulose by a catalytic membrane described herein.

Methods described herein, in some embodiments, further comprise passing the glucose, reducing sugars or oligosaccharides or mixtures thereof through pores of the catalytic membrane to a permeate side of the membrane. In some embodiments, the method further comprises collecting the glucose, reducing sugars or oligosaccharides or mixtures thereof on the permeate side of the membrane. In some embodiments wherein the catalytic membrane is a nanofiltration membrane, only glucose, reducing sugars and/or other monomeric sugar species are passed to the permeate side of the membrane. Additionally, in some embodiments, hemicellulose is hydrolyzed by the acidic functionalities of the membrane into various products including glucose, xylose, mannose, galactose, arabinose or mixtures thereof.

In another aspect, methods of making catalytic membranes are described herein. In some embodiments, a method of making a catalytic membrane comprises grafting a polymer onto a surface of the membrane. The polymer comprises cellulose solubilization functionalities and acid functionalities for the catalytic hydrolysis of cellulose and/or hemicellulose. In some embodiments, grafting comprises providing monomer comprising a cellulose solubilization functionality or cellulose solubilization functionality precursor and polymerizing the monomer with a chemical species on the membrane surface. Moreover, in some embodiments, the method further comprises functionalizing at least a portion of the repeating units of the resulting polymer with an acid functionality for the catalytic hydrolysis of cellulose and/or hemicellulose.

In another aspect, a method of making a catalytic membrane comprises attaching cellulose hydrolysis chemical species onto a surface of the membrane and grafting cellulose solubilization polymer onto the surface of the membrane. Attaching cellulose hydrolysis chemical species onto a membrane surface, in some embodiments, comprises grafting cellulose hydrolysis polymer onto the membrane surface. Grafting cellulose hydrolysis polymer onto a surface of the membrane can comprise functionalizing the membrane surface with polymerization initiator for monomer of the hydrolysis polymer and conducting polymerization of the monomer in the presence of the initiator. Additionally, in some embodiments, grafting cellulose solubilization polymer onto a surface of the membrane comprises functionalizing the membrane surface with polymerization initiator for monomer of the solubilization polymer and conducting polymerization of the monomer in the presence of the initiator. In some embodiments, initiator for monomer of the hydrolysis polymer is different than initiator for monomer of the solubilization polymer.

These and other embodiments are described in greater detail in the detailed description which follows.

DETAILED DESCRIPTION

Figure 1:
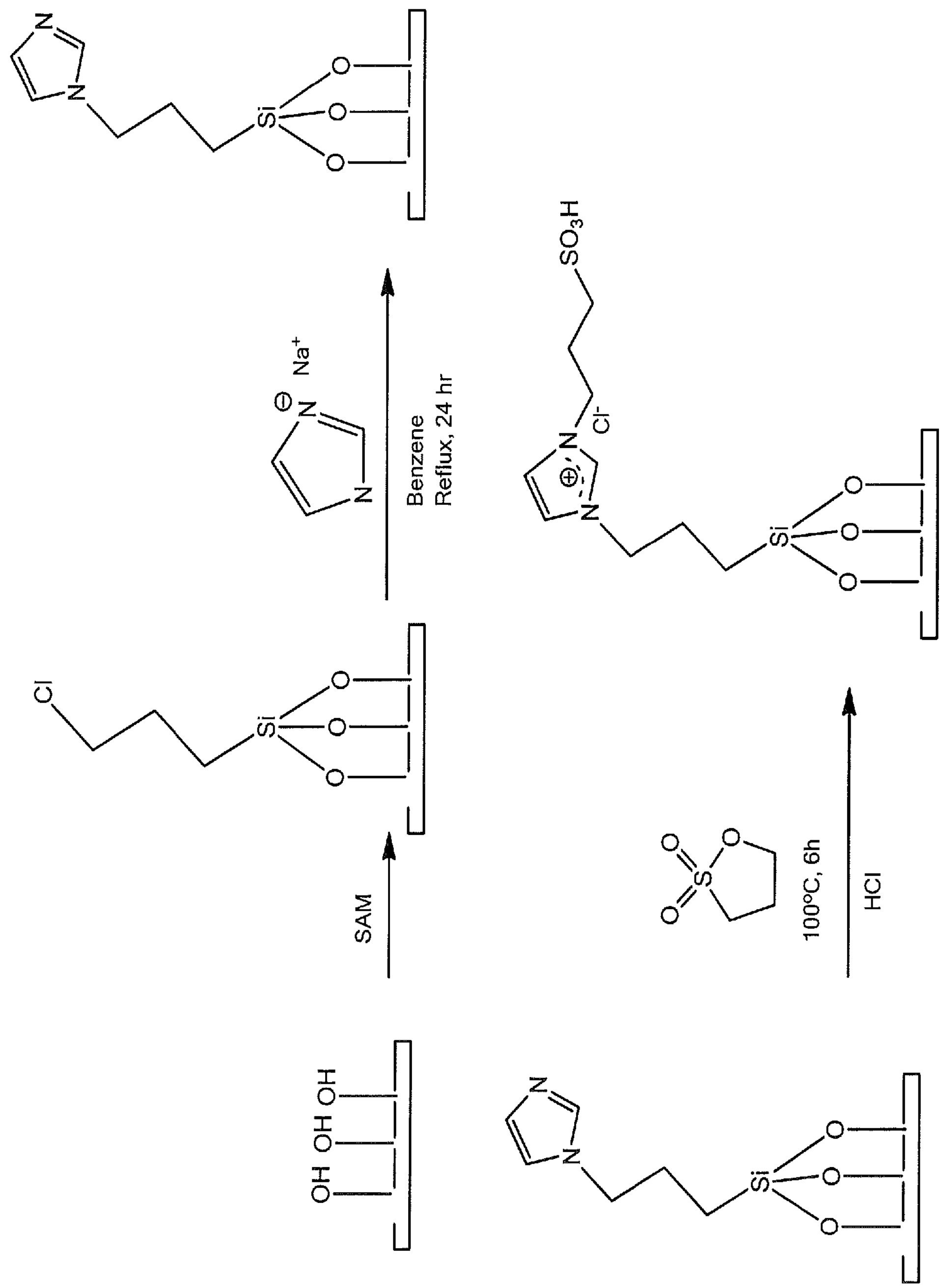
FIG. 1 illustrates a reaction scheme for functionalizing a membrane surface with an ionic liquid having acid functionality according to one embodiment described herein.

Embodiments described herein can be understood more readily by reference to the following detailed description, examples, and drawings. Elements, apparatus, and methods described herein, however, are not limited to the specific embodiments presented in the detailed description, examples, and drawings. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

I. Catalytic Membranes

In one aspect, catalytic membranes operable for the hydrolysis of cellulose and/or hemicellulose are described herein. In some embodiments, a catalytic membrane comprises a surface functionalized with a polymer, the polymer comprising cellulose solubilization functionalities and acid functionalities for the catalytic hydrolysis of cellulose and/or hemicellulose. In some embodiments, the surface of a catalytic membrane described herein is further functionalized with additional acid functionalities that are not part of the polymer, the additional acid functionalities operable for the catalytic hydrolysis of cellulose and/or hemicellulose.

In another aspect, a catalytic membrane comprises a surface functionalized with cellulose solubilization polymer and one or more cellulose hydrolysis chemical species. Cellulose solubilization polymer comprises cellulose solubilization functionalities, such as one or more imidazolium salts. Cellulose hydrolysis chemical species comprise one or more acid functionalities for the catalytic hydrolysis of cellulose and/or hemicellulose. In some embodiments, for example, cellulose hydrolysis chemical species comprise cellulose hydrolysis polymer comprising one or more acid functionalities for the catalytic hydrolysis of cellulose. Cellulose hydrolysis chemical species, in other embodiments, comprise non-polymeric species having one or more acid functionalities for the catalytic hydrolysis of cellulose. Further, in some embodiments, a catalytic membrane comprises a surface functionalized with cellulose hydrolysis chemical species without co-functionalization with cellulose solubilization polymer.

A functionalized membrane surface can comprise any desired membrane surface. In some embodiments, the surface is a pore surface of the membrane. In some embodiments, the surface is a first side of the membrane for receiving cellulose feedstock. The first side, in some embodiments, is a retentate side of the membrane. The membrane can also comprise a permeate side. In some embodiments, the membrane comprises a second side in facing opposition to the first side, wherein the second side is not functionalized with cellulose solubilization or hydrolysis chemical species. The second side, in some embodiments, is a permeate side of the membrane. Further, the first and second sides can be planar or curved.

Catalytic membranes described herein can have any dimensions and shape not inconsistent with the objectives of the present invention. In some embodiments, the dimensions and/or shape of a catalytic membrane are selected to optimize the efficiency and throughput of the catalytic membrane. In some embodiments, for example, the dimensions of the catalytic membrane are suitable for the efficient transport of glucose, reducing sugars and/or oligosaccharides of desired molecular weight across the membrane. In some embodiments wherein hemicellulose is hydrolyzed, the dimensions of the catalytic membrane are suitable for the efficient transport of glucose, xylose, mannose, galactose, arabinose or oligosaccharides or mixtures thereof. A catalytic membrane, in some embodiments, has dimensions suitable for use in industrial applications.

In some embodiments, the thickness of a catalytic membrane described herein is selected according several considerations including, but not limited to, a suitable diffusion path length for glucose, reducing sugars and/or oligosaccharides passing through the membrane, the desired mechanical strength of the membrane and any desired rheological and/or deformation properties of the membrane. A catalytic membrane described herein, in some embodiments, has a thickness less than about 5 mm. In some embodiments, a catalytic membrane has a thickness less than about 3 mm or less than about 1 mm. In some embodiments, a catalytic membrane has a thickness ranging from about 1 mm to about 10 mm or from about 1 mm to about 5 mm.

Moreover, in some embodiments, a catalytic membrane described herein has a planar or substantially planar shape, such as a disk shape or a sheet shape. Alternatively, in some embodiments, a catalytic membrane described herein is tubular. In some embodiments, for instance, the interior of a tubular catalytic membrane is a permeate side of the membrane, and the exterior of the tubular catalytic membrane is a retentate side of the membrane. In other embodiments, the exterior of a tubular catalytic membrane is a permeate side and the interior of the tubular catalytic membrane is a retentate side.

Further, in some embodiments, catalytic membranes described herein can be disposed in an array. For example, in some embodiments, a plurality of tubular catalytic membranes can be disposed in an array. The membranes of the array can be used cooperatively. In some embodiments, for instance, the interiors of the tubular catalytic membranes of the array can be retenate sides for receiving a cellulose feedstock, and the exteriors can be permeate sides for receiving sugar reaction products. Alternatively, the exteriors of the tubular catalytic membranes of the array can be retenate sides for receiving a cellulose feedstock, and the interiors can be permeate sides for receiving sugar reaction products.

Catalytic membranes described herein can be formed of any material not inconsistent with the objectives of the present invention. In some embodiments, a material of a catalytic membrane is selected according to the ability of the material to be functionalized with a surface polymer as described further herein. In some embodiments, a catalytic membrane comprises an inorganic composition. An inorganic composition, in some embodiments, comprises a ceramic. In some embodiments, for example, a catalytic membrane is formed of one or more of alumina ($Al_2O_3$), silica ($SiO_2$), titania ($TiO_2$) and zirconia ($ZrO_2$).

A catalytic membrane, in some embodiments, comprises an organic composition. In some embodiments, for example, a catalytic membrane is formed of a polymeric composition. In some embodiments, suitable polymers for the membrane are operable to be functionalized with a surface polymer described herein and demonstrate chemical, thermal and mechanical stabilities required for cellulose hydrolytic processes. In some embodiments, a catalytic membrane is formed from polyvinyl alcohol, polyvinyl chloride or polyacrylonitrile. In some embodiments, a catalytic membrane is formed of oxygen plasma treated or oxygen plasma modified polymer. In some embodiments, for example, a catalytic membrane is formed of oxygen plasma treated polyolefin, such as polyethylene or polypropylene. A catalytic membrane, in some embodiments, is formed of oxygen plasma treated polystyrene. Oxygen plasma treatment of polymeric materials forming catalytic membranes, in some embodiments, can provide the polymeric materials moieties suitable for surface functionalization with a polymer having cellulose solubilization functionalities and acidic functionalities described herein.

In some embodiments, a catalytic membrane comprises an inorganic composition and an organic composition. In one embodiment, for example, a catalytic membrane is formed of a polymer coated metal or polymer coated ceramic.

A catalytic membrane, in some embodiments, is porous. Pores of a catalytic membrane can have any size not inconsistent with the objectives of the present invention. In some embodiments, a membrane has a pore size sufficient to pass glucose molecules, reducing sugar molecules and/or oligosaccharides resulting from the catalytic hydrolysis of cellulose conducted by the membrane. In some embodiments, pores of the membrane have a size operable to exclude oligosaccharide molecules in excess of 500 g/mol or 300 g/mol. In some embodiments, pores of the membrane have a size operable to exclude lignin, hemicellulose and/or cellulose. A membrane, in some embodiments, has a molecular weight cutoff (MWCO) of less than about 3 kD. In some embodiments, the MWCO is less than about 2 kD. In some embodiments, the MWCO ranges from about 1 kD to about 3 kD. The MWCO, in some embodiments, ranges from about 100 Da to 3000 Da or from about 100 Da to 500 Da.

A catalytic membrane having a construction described herein, in some embodiments, is a nanofiltration membrane having a pore size distribution less than about 100 nm. In some embodiments, a nanofiltration catalytic membrane has a pore size distribution less than about 50 nm or less than about 20 nm. A nanofiltration catalytic membrane described herein, in some embodiments has a pore size distribution ranging from about 0.5 nm to about 15 or from about 1 nm to about 10 nm.

Pore size distribution of a catalytic membrane described herein, in some embodiments, is controlled or tailored by species bound to surfaces of the catalytic membrane. For example, in some embodiments, pore size distribution of the catalytic membrane is controlled or tailored by one or more polymeric species functionalizing surfaces of the membrane. The one or more polymeric species can include polymer comprising cellulose solubilization functionalities and acid functionalities for the catalytic hydrolysis of cellulose. In some embodiments, the one or more polymeric species can include cellulose solubilization polymer and/or cellulose hydrolysis polymer.

Accordingly, in some embodiments, pores of a catalytic membrane described are functionalized. For example, pores of the membrane can be functionalized with acid functionalities for the catalytic hydrolysis of cellulose and/or oligosaccharides. In some embodiments, pores of the catalytic membrane are functionalized with cellulose hydrolysis polymer or non-polymeric species having acid functionalities for the catalytic hydrolysis of cellulose. In some embodiments, pores of a catalytic membrane are functionalized with polymer described herein comprising cellulose solubilization functionalities and acid functionalities for the catalytic hydrolysis of cellulose and/or hemicellulose. Therefore, a catalytic membrane described herein can be operable to further hydrolyze one or more species passing through the pores, such one or more oligosaccharide molecules.

A catalytic membrane described herein, in some embodiments, is symmetric or asymmetric. An asymmetric membrane can have chemical and/or physical characteristics that change in the direction of the body thickness.

As described herein, polymer functionalizing one or more surfaces of the membrane can comprise cellulose solubilization functionalities and acid functionalities for the catalytic hydrolysis of cellulose. In some embodiments, cellulose solubilization functionalities of the polymer are operable to at least partially solubilize cellulose. In some embodiments, for example, the cellulose solubilization functionalities of the polymer comprise one or more imidazolium salts. In some embodiments, the one or more imidazolium salts is of the formula:

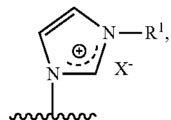

wherein ~~~ is a point of attachment to the polymer chain, $X^-$ is a counterion and $R^1$ is selected from the group consisting of hydrogen, alkyl, alkyl-sulfonic acid, alkyl-carboxylic acid and alkyl-phosphonic acid. Any counterion not inconsistent with the objectives of the present invention may be used. In some embodiments, the one or more imidazolium salts comprise imidazolium chlorides.

In some embodiments of catalytic membranes described herein, the cellulose solubilization functionalities are at least partially hydrophobic and operable to exclude or substantially exclude water. Moreover, in some embodiments, cellulose solubilization functionalities are also operable to at least partially solubilize hemicellulose.

The surface functionalizing polymer described herein also comprises acid functionalities for the catalytic hydrolysis of cellulose and/or hemicellulose. In some embodiments, suitable acid functionalities have a pKa ranging from about 1 to about 5. In some embodiments, suitable acid functionalities have a pKa ranging from about 1 to about 3 or from about 3 to about 5. In some embodiments, suitable acid functionalities comprise sulfonic acid, carboxylic acid or phosphonic acid functionalities or mixtures thereof. Additionally, in some embodiments, the surface of a catalytic membrane is further functionalized with acid functionalities that are not part of the polymer, as described further herein. The additional acid functionalities can be the same or different as the acid functionalities of the polymer.

Moreover, the surface functionalizing polymer can comprise any arrangement of cellulose solubilization functionalities and acid functionalities. In some embodiments, for instance, at least one of the cellulose solubilization functionalities is functionalized with at least one of the acid functionalities for the catalytic hydrolysis of cellulose. In some embodiments, the polymer comprises a block of repeating units comprising the cellulose solubilization functionalities and a block of repeating units comprising the acid functionalities. Blocks of repeating units comprising the cellulose solubilization functionalities and the acid functionalities can have various arrangements. In some embodiments, a diblock copolymer is formed from a block of repeating units comprising cellulose solubilization functionalities and a block of repeating units comprising acid functionalities. In some embodiments, an additional block of repeating units comprising cellulose solubilization functionalities or acid functionalities is provided resulting in a triblock copolymer. A tetrablock copolymer, in some embodiments, is provided by two blocks of repeating units comprising cellulose solubilization functionalities alternating with two blocks of repeating units comprising acid functionalities. In some embodiments, a multiblock copolymer is provided by multiple blocks of repeating units comprising cellulose solubilization functionalities and multiple blocks of acid functionalities.

In some embodiments, a block of repeating units comprising cellulose solubilization functionalities is distal to the surface of the membrane. In other embodiments, a block of repeating units comprising cellulose solubilization functionalities is proximate to the surface of the membrane. In some embodiments, repeating units comprising cellulose solubilization functionalities and repeating units comprising acid functionalities are arranged relative to one another so as to create a pH gradient and/or maximize cellulose solubilization and hydrolysis.

Alternatively, in some embodiments, a polymer described herein comprises a random distribution of repeating units comprising cellulose solubilization functionalities and repeating units comprising acid functionalities. In some embodiments, a polymer comprises a statistical distribution of repeating units comprising cellulose solubilization functionalities and repeating units comprising acid functionalities. In some embodiments, a polymer comprises an alternating distribution of repeating units comprising cellulose solubilization functionalities and repeating units comprising acid functionalities. In some embodiments, the distribution of repeating units in a surface functionalizing polymer is selected to optimize the efficiency and/or reaction rate of the catalytic membrane.

A surface functionalizing polymer comprising cellulose solubilization functionalities and acid functionalities for the catalytic hydrolysis of cellulose can have any desired chain length. Chain lengths of a surface functionalizing polymer can be selected according to several considerations including, but not limited to, effective solubilization of cellulose contacting the membrane, efficient hydrolysis of the cellulose into the reaction products of glucose, reducing sugars and/or oligosaccharides and the diffusion time of such reaction products through the surface polymer layer and membrane. Moreover, the membrane surface can have any desired density of functionalizing polymer chains. The density of functionalizing polymer chains can be selected according to several considerations including, but not limited to, the effective solubilization of cellulose contacting the membrane and efficient hydrolysis of the cellulose into the reaction products of glucose, reducing sugars and/or oligosaccharides for passage through the membrane.

In some embodiments, a surface functionalizing polymer described herein is an ionic liquid.

In another aspect, a catalytic membrane described herein comprises a surface functionalized with cellulose solubilization polymer and one or more cellulose hydrolysis chemical species. Cellulose solubilization polymer comprises cellulose solubilization functionalities, such as one or more imidazolium salts. In some embodiments, one or more imidazolium salts of cellulose solubilization polymer is of the formula:

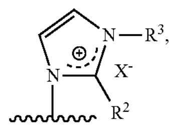

wherein ~~~ is a point of attachment to the polymer chain, $X^-$ is a counterion and $R^2$ and $R^3$ are independently selected from the group consisting of -hydrogen and -alkyl. Any counterion not inconsistent with the objectives of the present invention may be used. In some embodiments, the one or more imidazolium salts comprise imidazolium chlorides.

Cellulose solubilization functionalities of the solubilization polymer, in some embodiments, are at least partially hydrophobic and operable to exclude or substantially exclude water during interaction with cellulose. Further, cellulose solubilization functionalities, in some embodiments, are operable to at least partially solubilize hemicellulose. Cellulose solubilization polymer can have any desired chain length. Chain length of cellulose solubilization polymer can be selected according to several considerations including, but not limited to, effective solubilization of cellulose contacting functionalized surfaces of the membrane, sufficient access of solubilized cellulose to hydrolysis chemical species on the membrane surface and efficient passage of cellulose hydrolysis product(s) through the membrane pore structure for collection.

Cellulose solubilization polymer, in some embodiments, does not comprise acid functionalities for the catalytic hydrolysis of cellulose and/or hemicellulose. The catalytic hydrolysis of cellulose is administered by one or more independent cellulose hydrolysis chemical species functionalizing the membrane surface. In some embodiments, cellulose hydrolysis chemical species comprises cellulose hydrolysis polymer. Cellulose hydrolysis polymer includes polymeric species comprising one or more acid functionalities for the catalytic hydrolysis of cellulose and/or hemicellulose. Suitable acid functionalities of cellulose hydrolysis polymer can have a pKa ranging from about 1 to about 5. In some embodiments, suitable acid functionalities have a pKa ranging from about 1 to about 3 or from about 3 to about 5. Suitable acid functionalities, in some embodiments, comprise sulfonic acid, carboxylic acid or phosphonic acid functionalities or combinations thereof.

Cellulose hydrolysis polymer, in some embodiments, comprises polystyrene sulfonic acid (PSSA) or poly(vinyl benzoic acid). Aromatic rings of hydrolysis polymer, such as PSSA and poly(vinyl benzoic acid), can be substituted with hydroxyl moieties, halogen atoms, including fluorine and chlorine, to further enhance interaction with cellulose. Use of aromatic structures in the hydrolysis polymer can assist in dehydrating surfaces of cellulose interacting with the catalytic membrane, thereby reducing the barrier for hydrolysis. Additionally, in some embodiments, non-aromatic cellulose hydrolysis polymer can be employed, such as poly(vinyl sulfonic acid)

Cellulose hydrolysis polymer can have any desired chain length. Chain length of cellulose hydrolysis polymer can be selected according to several considerations including, but not limited to, effective hydrolysis of cellulose and/or hemicellulose, sufficient access of cellulose to solubilization polymer on the membrane surface and efficient passage of cellulose hydrolysis product(s) through the membrane pore structure for collection.

Moreover, in some embodiments, cellulose hydrolysis chemical species functionalizing a membrane surface are non-polymeric. Non-polymeric cellulose hydrolysis chemical species, in some embodiments, comprise ionic liquids having acidic functionalities. For example, in some embodiments, non-polymeric cellulose hydrolysis chemical species comprise imidazolium salts having acidic functionalities. A catalytic membrane described herein, in some embodiments, is functionalized with a sulfonated imidazolium salt according to FIG. 1.

Cellulose solubilization polymer and cellulose hydrolysis chemical species can be provided on a membrane surface in any desired ratio. The ratio of solubilization polymer to hydrolysis chemical species on a membrane surface can be selected according to several considerations including, but not limited to, the specific identities of the solubilization polymer and hydrolysis chemical species, sufficient solubilization and hydrolysis of cellulose in contact with the functionalized membrane surface and efficient passage of cellulose hydrolysis product(s) through the membrane pore structure for collection.

The ratio of cellulose solubilization polymer to cellulose hydrolysis chemical species on a membrane surface, in some embodiments, ranges from 1:1 to 1:10. The ratio of cellulose solubilization polymer to cellulose hydrolysis chemical species, in some embodiments, can be selected from Table I.

TABLE I

| Surface Ratio of Solubilization Polymer to Hydrolysis Species |
|---|
| Cellulose Solubilization Polymer/Cellulose Hydrolysis Chemical Species |
| 1:1.5 |
| 1:2 |
| 1:3 |
| 1:4 |
| 1:5 |

Further, in some embodiments, a catalytic membrane described herein comprises a surface functionalized with cellulose hydrolysis chemical species without co-functionalization with cellulose solubilization polymer. For example, a membrane surface, in some embodiments, is functionalized with cellulose hydrolysis polymer without the presence of cellulose solubilization polymer. In such embodiments, cellulose solubilization can be addressed in a liquid phase in which the cellulose feedstock is disposed. As described further herein, liquid phase for the cellulose can be an ionic liquid or a mixture of ionic liquid and water.

Additionally, catalytic membranes described herein, in some embodiments, are stable in harsh environments, such as high temperature and/or low pH (acidic) environments used in the conversion of lignocellulosic materials to fermentable sugars. In some embodiments, for example, a catalytic membrane described herein is stable in an environment having a pH less than about 5. In some embodiments, a catalytic membrane is stable in an environment having a pH less than about 3 or less than about 2. In some embodiments, a catalytic membrane is stable in an environment having a pH between about 1 and about 5.

Further, in some embodiments, a catalytic membrane is stable at a temperature of at least about 100° C. In some embodiments, a catalytic membrane is stable at a temperature up to about 200° C. or up to about 300° C. In some embodiments, a catalytic membrane is stable at a temperature ranging from about 0° C. to about 200° C. or from about 0° C. to about 300° C.

In being stable at one or more of the foregoing pH values and/or temperatures, a catalytic membrane described herein does not demonstrate any significant chemical and/or physical degradation including, but not limited to, the loss of surface functionalizing polymer, erosion of the membrane surface and loss of pore structure due to plastic deformation or membrane dissolution.

In addition, catalytic membranes described herein, in some embodiments, have sufficient mechanical strength to withstand pressurizing and/or backflushing. A catalytic membrane described herein can be subjected to the application of pressure on the retentate side of the membrane to assist in driving cellulose hydrolysis product(s) across the membrane. In some embodiments, a catalytic membrane having a construction described in this Section I is operable to withstand pressures ranging from 1 to 50 bar or from 5 to 25 bar. Further, backflushing, in some embodiments, can include backflushing to dislodge particles from surfaces and/or pores of the catalytic membrane, such as lignin particles.

II. Membrane Reactors

In another aspect, membrane reactors are described herein. In some embodiments, a membrane reactor comprises a feedstock vessel, a reaction product collection vessel, and a catalytic membrane disposed between the feedstock vessel and the reaction product collection vessel. The catalytic membrane can have any construction and/or properties described in Section I herein. In some embodiments, for example, the catalytic membrane comprises a feedstock contacting surface functionalized with a polymer, the polymer comprising cellulose solubilization functionalities and acid functionalities for the catalytic hydrolysis of cellulose and/or hemicellulose. Alternatively, in some embodiments, a feedstock contacting surface of the catalytic membrane is functionalized with cellulose solubilization polymer and one or more cellulose hydrolysis chemical species. Additionally, in some embodiments, a feedstock contacting surface of the catalytic membrane can be functionalized with cellulose hydrolysis chemical species without co-functionalization with cellulose solubilization polymer.

Therefore, membrane reactors described herein, in some embodiments, are operable to convert feedstock comprising cellulose into sugar reaction product. The sugar reaction product, in some embodiments, comprises glucose, reducing sugars or oligosaccharides or mixtures thereof. In some embodiments, membrane reactors described herein are compatible with chemical pretreatment steps comprising the removal and/or decomposition of lignin from lignocellulosic materials.

Turning now to components of membrane reactors described herein, a membrane reactor described herein comprises a feedstock vessel. Any feedstock vessel not inconsistent with the objectives of the present invention may be used. In some embodiments, a feedstock vessel contains or stores one or more lignocellulosic materials. Lignocellulosic materials, in some embodiments, comprise one or more types of wood. In some embodiments, for example, wood comprises hardwood, softwood or mixtures thereof. In some embodiments, wood comprises one or more types of genetically modified woods or plants. In some embodiments, a lignocellulosic material comprises plant leaves and/or stalks including, but not limited to, corn stover. Moreover, in some embodiments, lignocellulosic material comprises one or more grasses including, but not limited to, switchgrass. Lignocellulosic material suitable for use in membrane reactors described herein, in some embodiments can be obtained as waste products from various applications such as timber harvesting and associated processing, agricultural harvesting and associated processing and/or landscape clearing and maintenance applications. A feedstock vessel, in some embodiments, comprises cellulose, xylan in addition to lignocellulosic material.

In some embodiments, the lignocellulosic material in a feedstock vessel is in one or more stages of decomposition. A lignocellulosic material, for example, can be in a state of decomposition wherein lignin is being removed or decomposed for the liberation of cellulose and/or hemicellulose. In some embodiments, a feedstock vessel contains a mixture of lignin, xylan, hemicellulose and cellulose.

Alternatively, in some embodiments, a feedstock vessel contains filtered cellulose, hemicellulose or mixtures thereof. In some embodiments, a reaction mixture comprising decomposed lignocellulosic material is filtered or otherwise subjected to separation procedure(s) to isolate cellulose, hemicellulose or mixtures thereof. The isolated cellulose of hemicellulose can be provided to the feedstock vessel for interaction with a catalytic membrane described herein.

A feedstock vessel of a membrane reactor described herein can comprise a liquid phase in which lignocellulosic material, hemicellulose, xylan and/or cellulose is disposed. The liquid phase, in some embodiments, comprises an ionic liquid, water or a mixture of ionic liquid and water. Ionic liquid for the liquid phase can comprise one or more imidazolium salts, such as imidazolium chlorides. Suitable imidazolium salts, in some embodiments, are of formula:

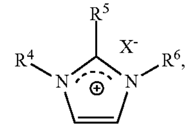

wherein $R^4$ and $R^6$ are independently selected from the group consisting of -alkyl and -alkenyl and $R^5$ is selected from the group consisting of -hydrogen and -alkyl. Suitable ionic liquids can comprise 1-alkyl(R)-3-methylimidazolium salts, 1-alkyl(R)-2,3-dimethylimidazolium salts or mixtures thereof.

Ionic liquid can be mixed with water to provide a liquid phase of a feedstock vessel in some embodiments described herein. Ionic liquid, such as imidazolium salt(s), can be present in a mixture with water in any desired amount. In some embodiments, ionic liquid is present in a mixture with water according to Table II.

TABLE II

| Ionic Liquid/$H_2O$ Mixture |
|---|
| Volume Percent Ionic Liquid |
| ≤90 |
| ≤70 |
| ≤50 |
| 5-95 |
| 10-80 |
| 20-60 |
| 5-50 |
| 1-50 |
| 10-20 |

In some embodiments wherein an ionic liquid/$H_2O$ mixture serves a liquid phase in the feedstock vessel, a nanofiltration catalytic membrane is employed, thereby blocking the passage of ionic liquid to the permeate side of the membrane. Ionic liquid of the liquid phase, therefore, is preserved and can be reused in subsequent cycles of lignocellulosic material processing for cellulose hydrolysis. In some embodiments of a nanofiltration membrane, only water, glucose, reducing sugars and/or other monomeric sugar species are passed to the permeate side of the membrane.

Further, a feedstock vessel described herein can have any desired size and shape. In some embodiments, a feedstock vessel has a size suitable for use in industrial applications.

A membrane reactor described herein also comprises a reaction product collection vessel. In some embodiments, a reaction product collection vessel contains an organic phase for extraction of sugar reaction product passing through the membrane. In some embodiments, an organic phase is a strip solution. A strip solution, in some embodiments, is operable to precipitate at least a portion of the sugar reaction product. In some embodiments, a reaction product collection vessel comprises boronic acid or a boronic acid derivative.

In some embodiments, a reaction product collection vessel described herein comprises a sugar collector. A sugar collector, in some embodiments, is operable to isolate glucose and/or other reducing sugars from other species in the reaction product collection vessel. For example, in some embodiments, a sugar collector comprises a nanofiltration membrane.

A reaction product collection vessel described herein can have any desired size. In some embodiments, a reaction product collection vessel has a size suitable for use in industrial applications.

As described herein, a membrane reactor also comprises a catalytic membrane disposed between the feedstock vessel and the reaction product collection vessel. The catalytic membrane can comprise any construction and properties, including any surface functionalizing polymer or chemical species, described in Section I hereinabove.

III. Methods of Cellulose Hydrolysis

In another aspect, methods for the hydrolysis of cellulose are described herein. In some embodiments, a method for the hydrolysis of cellulose comprises providing a cellulose feedstock and bringing the cellulose feedstock into contact with a surface of a catalytic membrane. The surface of the membrane, in some embodiments, is functionalized with a polymer comprising cellulose solubilization functionalities and acid functionalities for the catalytic hydrolysis of the cellulose. The cellulose feedstock is at least partially solubilized with the cellulose solubilization functionalities, and the solubilized cellulose is hydrolyzed with the acid functionalities to provide glucose, reducing sugars or oligosaccharides or mixtures thereof.

In some embodiments, the surface of the membrane in contact with the cellulose feedstock is functionalized cellulose solubilization polymer and one or more cellulose hydrolysis chemical species. The cellulose feedstock is at least partially solubilized with functionalities of the cellulose solubilization polymer, and the solubilized cellulose is hydrolyzed with the acid functionalities of the hydrolysis chemical species to provide glucose, reducing sugars or oligosaccharides or mixtures thereof. Further, in some embodiments, the membrane surface is functionalized with cellulose hydrolysis chemical species without co-functionalization with cellulose solubilization polymer.

In some embodiments, a method further comprises passing the glucose, reducing sugars or oligosaccharides or mixtures thereof through pores of the catalytic membrane to a permeate side of the membrane. Moreover, in some embodiments, a method further comprises hydrolyzing oligosaccharide molecules in the pores of the membrane. Additionally, a method described herein can further comprise collecting the glucose, reducing sugars or oligosaccharides or mixtures thereof on the permeate side of the membrane.

Turning now to specific steps of methods for the hydrolysis of cellulose, a method for the hydrolysis of cellulose described herein comprises providing a cellulose feedstock. A cellulose feedstock can comprise any source of cellulose not inconsistent with the objectives of the present invention. In some embodiments, a cellulose feedstock comprises a mixture of lignocellulosic material, xylan, hemicellulose and cellulose. Suitable lignocellulosic materials, in some embodiments, comprise those described in Section II hereinabove. Alternatively, in some embodiments, a cellulose feedstock comprises filtered cellulose, hemicellulose or mixtures thereof. In some embodiments, a reaction mixture comprising decomposed lignocellulosic material is filtered or otherwise subjected to separation procedure(s) to isolate the cellulose and/or hemicellulose feedstock.

Cellulose feedstock, in some embodiments, can be disposed in a liquid phase for interfacing with catalytic membranes described herein. A liquid phase, in some embodiments, comprises water, ionic liquid or a mixture of water and ionic liquid. In some embodiments, the presence of ionic liquid alone or in a mixture with water can assist in solubilizing lignocellulosic material in preparation for the hydrolysis of cellulose by a catalytic membrane described herein. A liquid phase comprising a mixture of ionic liquid and water can have any composition described in Section II herein, including an amount of ionic liquid in the mixture selected from Table II above. Further, suitable ionic liquids for the liquid phase can comprise imidazolium salts described in Section II herein.

Methods for the hydrolysis of cellulose described herein comprise bringing the cellulose feedstock into contact with a surface of a catalytic membrane. The catalytic membrane can comprise any construction and properties, including any surface functionalizing polymer or chemical species, described in Section I hereinabove.

Further, methods for the hydrolysis of cellulose described herein comprise at least partially solubilizing the cellulose feedstock and hydrolyzing the solubilized cellulose with acid functionalities of the functionalized membrane surface to provide glucose, reducing sugars or oligosaccharides or mixtures thereof. In some embodiments, solubilization and hydrolysis of cellulose is administered with a surface of the membrane functionalized with a polymer comprising cellulose solubilization functionalities and acid functionalities. Alternatively, cellulose solubilization can be administered by a first independent chemical species functionalizing the membrane surface, and cellulose hydrolysis can be administered by a second independent chemical species functionalizing the membrane surface. In such embodiments, cellulose solubilization polymer of the membrane surface solubilizes the cellulose while one or more cellulose hydrolysis chemical species hydrolyzes the cellulose. Cellulose solubilization polymer and cellulose hydrolysis chemical species functionalizing a membrane surface are described in Section I herein.

Additionally, in some embodiments of methods described herein, solubilization of lignocellulosic material and/or cellulose is provided by a liquid phase comprising ionic liquid or an aqueous ionic liquid mixture in the feedstock vessel, and cellulose hydrolysis is administered by one or more cellulose hydrolysis chemical species functionalizing the membrane surface. Therefore, in some embodiments described herein, the catalytic membrane is not functionalized with polymer or chemical species for the solubilization of cellulose. However, in some embodiments, cellulose solubilization species attached to a membrane described herein can be used in conjunction with a liquid phase comprising ionic liquid or an aqueous ionic liquid mixture for the solubilization of lignocellulosic material and/or cellulose.

In some embodiments wherein an ionic/mixture serves a liquid phase in the feedstock vessel, a nanofiltration catalytic membrane is employed thereby blocking the passage of ionic liquid to the permeate side of the membrane. Ionic liquid of the liquid phase is, therefore, preserved and can be reused in subsequent cycles of lignocellulosic material processing for cellulose hydrolysis. In some embodiments of a nanofiltration membrane, only water, glucose, reducing sugars and/or other monomeric sugar species are passed to the permeate side of the membrane.

Further, hydrolysis of cellulose described herein can be catalytic, permitting the catalytic membrane to be regenerated and/or reused. In some embodiments, the hydrolysis of the solubilized cellulose can be complete or substantially complete hydrolysis, providing glucose or reducing sugars or mixtures thereof. Alternatively, the hydrolysis of the solubilized cellulose can be partial hydrolysis, providing oligosaccharides.

A method for the hydrolysis of cellulose described herein can further comprise passing the glucose, reducing sugars or oligosaccharides or mixtures thereof through pores of the catalytic membrane to a permeate side of the membrane. In some embodiments, passing occurs immediately after hydrolysis. Passing immediately after hydrolysis can inhibit the degradation of the glucose and/or reducing sugars. Sugar degradation can be caused by harsh reaction conditions and/or various chemical species present on the retentate side of the membrane. In some embodiments, harsh reaction conditions can include high temperature and/or low pH. Passing glucose, reducing sugars or oligosaccharides or mixtures thereof through pores of the membrane, in some embodiments, is aided by application of pressure to the retentate side of the catalytic membrane. For example, in some embodiments, a pressure of 1-30 bar or 5-20 bar is applied to the retentate side of the membrane.

In some embodiments of a method described herein wherein oligosaccharides are passed through pores of a catalytic membrane, the method further comprises hydrolyzing oligosaccharide molecules in the pores of the membrane. In some embodiments, the oligosaccharide molecules in the pores of the membrane are hydrolyzed by acid functionalities attached to surfaces of the pores. In some embodiments, the hydrolysis of oligosaccharide molecules within the pores provides additional glucose or reducing sugars or mixtures thereof. The hydrolysis within the pores, in some embodiments, is catalytic.

A method described herein further comprises collecting the glucose, reducing sugars or oligosaccharides or mixtures thereof on the permeate side of the membrane. In some embodiments, collecting comprises extracting the glucose, reducing sugars or oligosaccharides or mixtures thereof into an organic phase. In some embodiments, for example, the organic phase comprises a boronic acid species, such as naphthalene-2-boronic acid.

In addition, in some embodiments, collecting comprises providing a sugar collector on the permeate side of the membrane. A sugar collector can be operable to isolate glucose and/or reducing sugars from other species on the permeate side of the membrane. For example, in some embodiments, a sugar collector comprises a nanofiltration membrane.

Further, in some embodiments, hemicellulose is hydrolyzed by the acidic functionalities of the polymer into various products including glucose, xylose, mannose, galactose, arabinose or mixtures thereof for passage through the membrane.

IV. Methods of Making a Catalytic Membrane

In another aspect, methods of making catalytic membranes are described herein. In some embodiments, a method of making a catalytic membrane comprises grafting a polymer onto a surface of the membrane, wherein the polymer comprises cellulose solubilization functionalities and acid functionalities for the catalytic hydrolysis of cellulose. Any of the polymer constructions described in Section I hereinabove comprising cellulose solubilization functionalities and acid functionalities may be used. Further, the surface onto which a polymer is grafted can comprise any desired membrane surface.

In some embodiments, grafting comprises providing monomer comprising a cellulose solubilization functionality or cellulose solubilization functionality precursor and polymerizing the monomer with a surface chemical species of the membrane. In some embodiments, for example, the monomer comprises a site of unsaturation, such as an alkene moiety. In some embodiments wherein the monomer comprises a site of unsaturation, polymerizing comprises free radical polymerization.

The surface chemical species of the membrane with which the polymerization is conducted can comprise any chemical moiety not inconsistent with the objectives of the present invention. In some embodiments, the surface chemical species comprises a polymerizable component, such as a carbon-carbon double bond. Moreover, the surface chemical species can be native to the membrane surface or added to the surface for purposes of grafting a polymer onto the surface. In some embodiments, the surface chemical species comprises an alkyl, aryl, alkenyl, haloalkyl, haloaryl, amino, or hydroxyl moiety or combinations thereof. In some embodiments, the surface chemical species comprises one or more species of silanes.

In addition, a method of making a catalytic membrane, in some embodiments, further comprises functionalizing at least a portion of the repeating units of the resulting polymer with an acid functionality for the catalytic hydrolysis of cellulose. Functionalizing at least a portion of the monomers can be carried out in any manner not inconsistent with the objectives of the present invention.

In another aspect, a method of making a catalytic membrane comprises attaching cellulose hydrolysis chemical species onto a surface of the membrane and grafting cellulose solubilization polymer onto the surface of the membrane. Attaching cellulose hydrolysis chemical species onto a membrane surface, in some embodiments, comprises grafting cellulose hydrolysis polymer onto the membrane surface. In some embodiments, grafting cellulose hydrolysis polymer onto a surface of the membrane comprises functionalizing the membrane surface with polymerization initiator for monomer of the hydrolysis polymer and conducting polymerization of the monomer in the presence of the initiator. Additionally, in some embodiments, grafting cellulose solubilization polymer onto a surface of the membrane comprises functionalizing the membrane surface with polymerization initiator for monomer of the solubilization polymer and conducting polymerization of the monomer in the presence of the initiator. In some embodiments, initiator for monomer of the hydrolysis polymer is different than initiator for monomer of the solubilization polymer.

Figure 2:
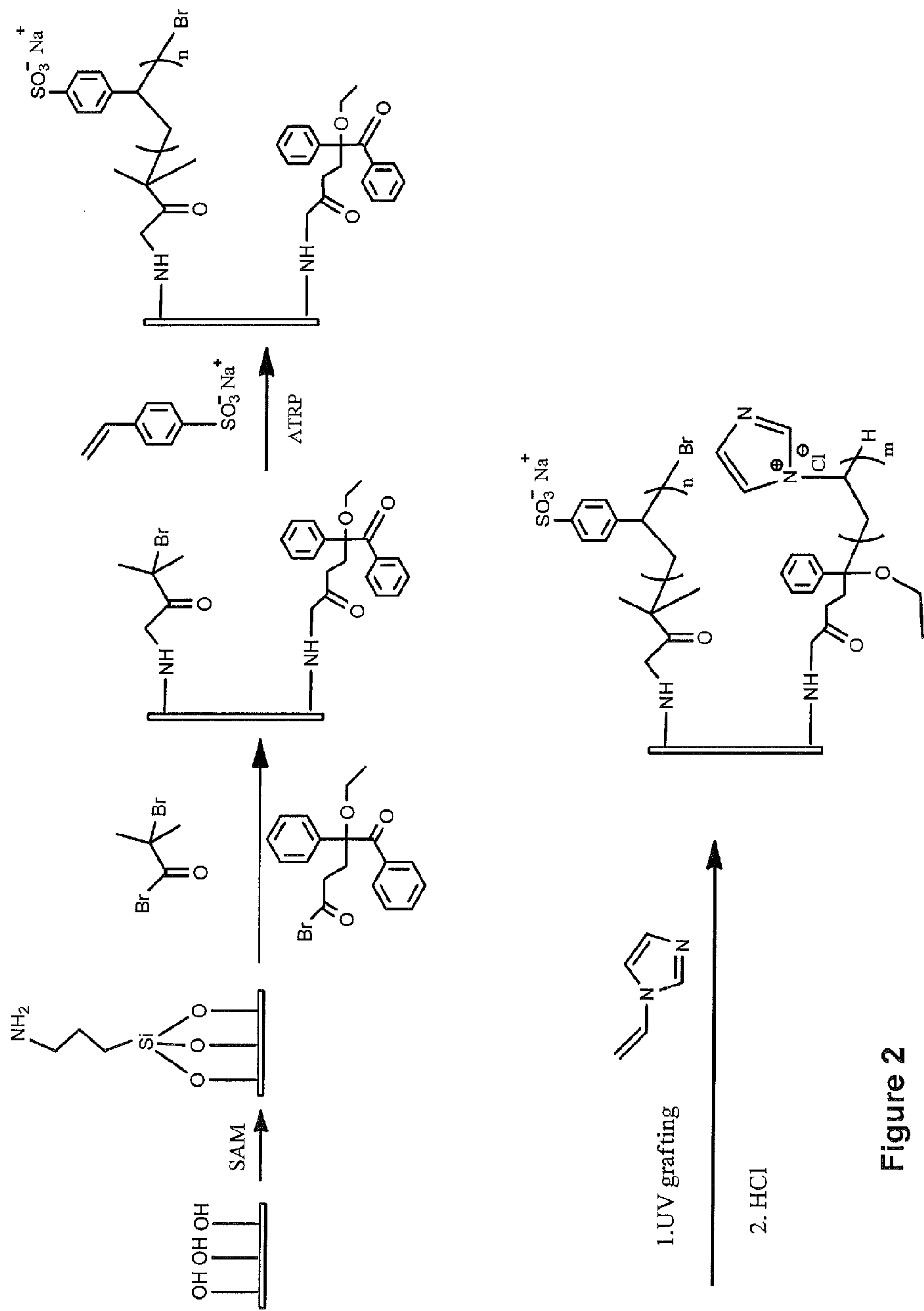
FIG. 2 illustrates a scheme for grafting cellulose hydrolysis polymer and cellulose solubilization polymer on a surface of a catalytic membrane according to one embodiment described herein.

FIG. 2 illustrates a scheme for grafting cellulose hydrolysis polymer and cellulose solubilization polymer on a surface of a catalytic membrane according to one embodiment described herein. As illustrated in FIG. 2, the membrane surface is initially functionalized with terminal amino-functionalities for the attachment of polymerization initiator (ATRP) for poly(styrene sulfonic acid) (PSSA) cellulose hydrolysis polymer and polymerization initiator (UV) for the poly(vinylimidazolium chloride) cellulose solubilization polymer. Membrane surface functionalization is administered by ATRP of sodium 4-styrenesulfonate followed by UV grating of N-vinyl imidazole. By using different initiators for polymerization, the ratio of cellulose hydrolysis polymer and cellulose solubilization polymer can be controlled.

In some embodiments, cellulose hydrolysis chemical species functionalizing a membrane surface are non-polymeric. Non-polymeric cellulose hydrolysis chemical species, in some embodiments, comprise ionic liquids having acidic functionalities. For example, in some embodiments, non-polymeric cellulose hydrolysis chemical species comprise imidazolium salts having acidic functionalities. A catalytic membrane described herein, in some embodiments, is functionalized with a sulfonated imidazolium salt according to FIG. 1.

Some embodiments described herein are further illustrated in the following non-limiting examples.

Example 1

Catalytic Membrane

Figure 3:
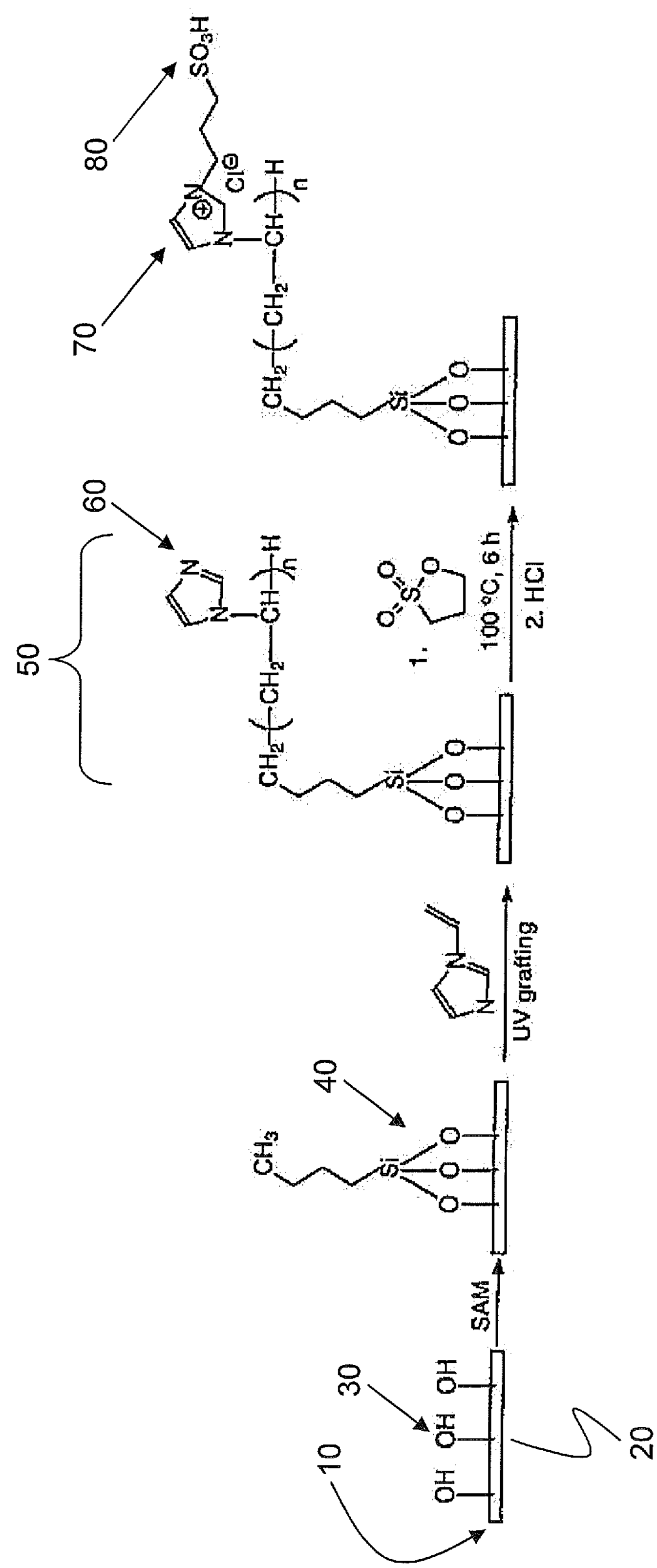
FIG. 3 illustrates a scheme for making a catalytic membrane according to one embodiment described herein.

A catalytic membrane according to one embodiment described herein was made as follows. With reference to FIG. 3, a surface (10) of a ceramic alumina, titania, zirconia (ATZ) membrane (20) obtained from Sterlitech Corporation of Kent, Wash., having surface hydroxyl groups (30) and a MWCO of 1 kD was functionalized with a self-assembled monolayer (SAM) (40, partially shown) by immersing the membrane (20) in a solution of trimethoxy(propyl)silane (5 mM in toluene) and refluxing for 24 h. The membrane (20) was then washed with toluene and dried. The membrane (20) was subsequently placed in a solution of benzophenone (BP) in methanol (1.82 g/L) for 1 h to adsorb BP to the membrane surface (10). N-vinylimidazole was then grafted to the SAM (40) on the membrane surface (10) using ultraviolet (UV) radiation. The membrane (20) was immersed in a solution of N-vinylimidazole in water (60 g/L) in a UV box and irradiated for 15 minutes, forming a polymer (50) comprising cellulose solubilization functionality precursors (60). Cellulose solubilization functionalities (70) and acid functionalities (80) were formed by sulfonating with 1,3-propanesultone in dry toluene at 100° C. for 6 h, followed by incubation in 36% w/w HCl solution for 24 h.

Figure 4:
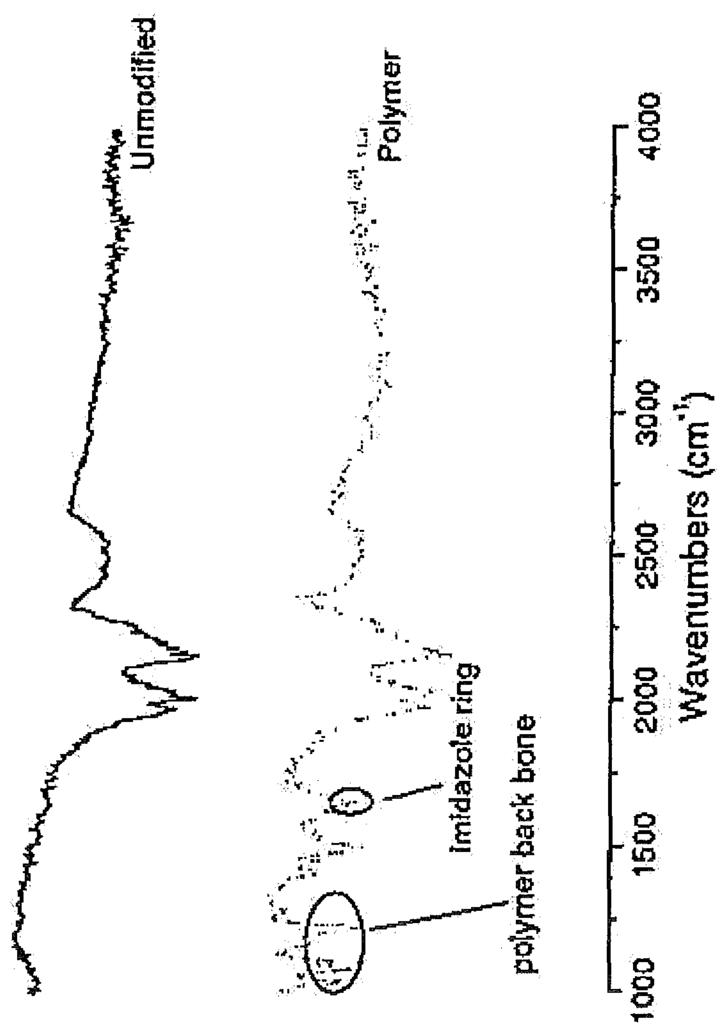
FIG. 4 illustrates infrared (IR) spectra of an unmodified ceramic membrane and a catalytic membrane according to one embodiment described herein.

The presence of polymer (50) on the membrane surface (10) was confirmed spectroscopically. FIG. 4 illustrates infrared (IR) spectra of an unmodified ceramic membrane and a membrane (20) functionalized with polymer (50). The spectra were collected using attenuated total reflectance (ATR) sampling in an FT-IR experiment.

To determine the acidic characteristics of the membrane (20), the membrane (20) was immersed in 50 mL water for 5 minutes. The pH of the solution was then measured, resulting in a value of 4.07.

Example 2

Cellulose Hydrolysis

Hydrolysis of cellulose using the catalytic membrane of Example 1 was tested. Cellulose (0.1 g) and 1-ethyl-3-methylimidazolium acetate (10 g) were added to a reaction vessel and heated to 120° C. After the cellulose dissolved, a small amount of water was added to the reaction vessel. The catalytic membrane of Example 1 was then placed in the solution. Next, the system was incubated at 120° C. for 4 h. The system was then cooled to room temperature and diluted with water to 100 mL. The glucose and total reducing sugar (TRS) concentrations in solution were then determined. The glucose concentration was determined using a Glucose Assay Kit (Sigma Aldrich). The TRS concentration was determined by 3,5-dinitrosalicylic acid (DNS) reagent, as described in C. Breuil and J. N. Saddler, "Comparison of the 3,5-dinitrosalicylic acid and Nelson-Somogyi methods of assaying for reducing sugars and determining cellulase activity," *Enzyme and Microb. Technol.,* 1985, 7, 327, the entirety of which is hereby incorporated by reference. The amount of unhydrolyzed cellulose was determined by lyophilizing. The measured amount of glucose was 5.23±0.51 mg, the amount of TRS was 32.06±1.08 mg, and the amount of unhydrolyzed cellulose was 61.26 mg.

Example 3

Cellulose Hydrolysis

Hydrolysis of cellulose using the catalytic membrane of Example 1 was tested. Cellulose (0.1 g) and 1-butyl-3-methylimidazolium chloride (10 g) were added to a reaction vessel and heated to 140° C. After the cellulose dissolved, a small amount of water was added to the reaction vessel. The catalytic membrane of Example 1 was then placed in the solution. Next, the system was incubated at 140° C. for 4 h. The system was then cooled to room temperature and diluted with water to 100 mL. The glucose and TRS concentrations in solution were then determined in accordance with Example 2. The amount of unhydrolyzed cellulose was determined by lyophilizing. The measured amount of glucose was 9.67 mg, the amount of TRS was 40.48 and the amount of unhydrolyzed cellulose was 54.37 mg.

Example 4

Cellulose Hydrolysis

Hydrolysis of cellulose using the catalytic membrane of Example 1 was tested. Cellulose (0.3 g), 1-butyl-3-methylimidazolium chloride (28.5 g) and water (1.5 g) were added to a reaction vessel and heated to 120° C. The catalytic membrane of Example 1 was then placed in the solution. Next, the system was incubated at 120° C. for the time periods set forth in Table IV. The system was then cooled to room temperature and diluted with water to 100 mL. The glucose and TRS concentrations in solution were then determined for each time period in accordance with Example 2. The amount of unhydrolyzed cellulose was determined by lyophilizing. The measured amounts of glucose, TRS and unhydrolyzed cellulose are provided in Table III.

TABLE III

| IL (g) | Water (g) | Cellulose (g) | Temperature (° C.) | Time (h) | TRS (mg) | Glucose (mg) |
|---|---|---|---|---|---|---|
| 28.5 | 1.5 | 0.3 | 120 | 2 | 20.58 | 3.64 |
| | | | | 4 | 29.40 | 4.92 |
| | | | | 8 | 37.29 | 5.59 |
| | | | | 10 | 38.36 | 5.71 |
| | | | | 24 | 40.25 | 4.01 |

Example 5

Hydrolysis and Diffusion in a Membrane Reactor

Figure 5:
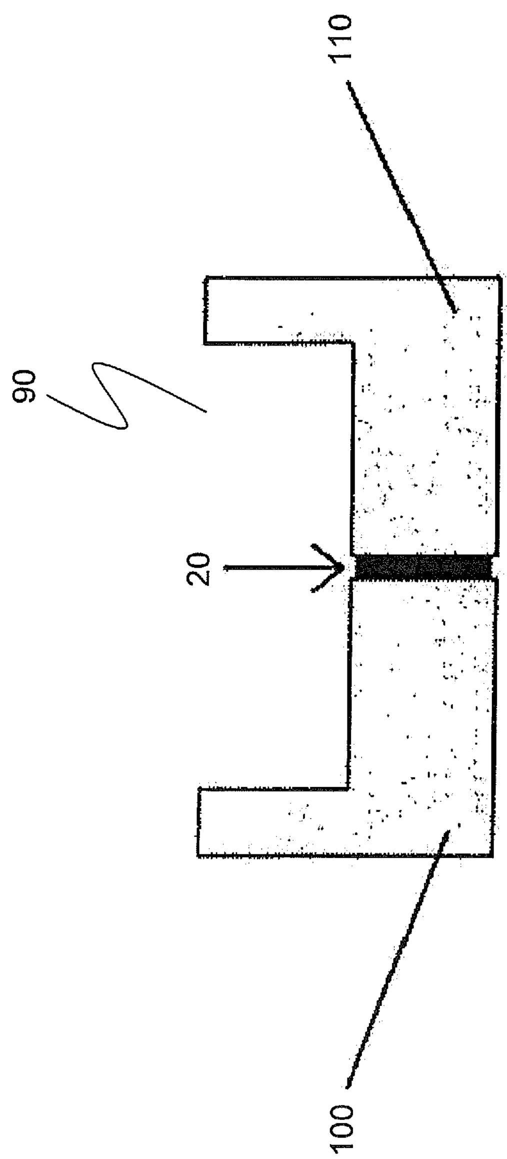
FIG. 5 illustrates a membrane reactor according to one embodiment described herein.

A membrane reactor according to one embodiment described herein was used to hydrolyze cellulose and diffuse glucose and reducing sugars (TRS) resulting from the hydrolysis across the catalytic membrane. With reference to FIG. 5, a membrane reactor (90) was prepared by sealing the catalytic membrane (20) of Example 1 in a diffusion cell, forming a feedstock vessel (100) and a collection vessel (110). 30 g of 1-ethyl-3-methylimidazolium acetate were added to each of the feedstock vessel (100) and the collection vessel (110). 0.3 g of cellulose was added to the feedstock vessel (100) and the membrane reactor (90) was then immersed in an oil bath at 90° C. and incubated for 4 h. The same protocol was performed for immersion times of 6 hours and 21 hours. The amount of glucose in each vessel (100, 110) was then measured. Cellulose not hydrolyzed in the experiments was regenerated by lyophilization and weighed. Table IV summarizes the results.

TABLE IV

| Sample | Temp (° C.) | IL (g) | Cellulose (g) | Time (h) | TRS-F[a] (mg) | TRS-P[a] (mg) | Glu-F[b] (mg) | Glu-P[b] (mg) | Cellulose Regenerated (mg) |
|---|---|---|---|---|---|---|---|---|---|
| 1 KD | 120 | 30[d] | 0.3[d] | 4 | 20.80 ± 0.56 | —[c] | 5.73 ± 0.14 | 1.63 ± 0.11 | 200.51 |
| | | | | 6 | 26.29 ± 0.38 | —[c] | 7.86 ± 0.16 | 3.24 ± 0.16 | |
| | | | | 21 | 61.47 ± 1.06 | 11.51 ± 0.99 | 1.67 ± 0.28 | 3.49 ± 0.01 | |

[a]total reducing sugar of feed (-F) and permeate (-P) side
[b]glucose on feed (-F) and permeate (-P) side
[c]not detected
[d]30 g on each side, 0.3 g cellulose on feed side As provided in Table IV, the catalytic membrane having a construction described herein hydrolyzed cellulose and passed a portion of the resulting glucose and reducing sugar reaction product to the permeate side for collection.

Example 6

Diffusion in a Membrane Reactor

A membrane reactor according to one embodiment described herein was used to pass glucose from a feedstock vessel to a collection vessel as follows. With reference to FIG. 5, a membrane reactor (90) was prepared by sealing the catalytic membrane (20) of Example 1 in a diffusion cell, forming a feedstock vessel (100) and a collection vessel (110). Water (70 mL) was added to each of the vessels (100, 110), and glucose (7 mg) was added to the feedstock vessel. The membrane reactor (90) was then immersed in an oil bath at 90° C. and incubated for 4, 7, or 24 h. The amount of glucose in each vessel (100, 110) was then measured. Table V summarizes the results.

TABLE V

| Time (h) | Glu in Feedstock Vessel (mg) | Glu in Collection Vessel (mg) |
|---|---|---|
| 4 | 5.68 ± 0.24 | 0.85 ± 0.05 |
| 7 | 5.17 ± 0.08 | 0.55 ± 0.07 |
| 24 | 4.61 ± 0.21 | None Detected |

As provided in Table V, the catalytic membrane having a construction described herein diffused glucose to the permeate side of the membrane.

Example 7

Catalytic Membrane

A catalytic membrane comprising surfaces functionalized with cellulose hydrolysis polymer and cellulose solubilization polymer according to one embodiment described herein was made as follows.

Synthesis of UV Initiator

The preparation procedures are presented in Scheme 1. Benzoin ethyl ether (BEE) (20 g) was dissolved in 32 mL DMSO containing potassium hydroxide (2 mL; 4 mol/L) and reacted with ethyl acrylate (8 mL) for 4 h under argon gas at room temperature. And then hydrochloric acid (8 mL; 1 mol/L) was added to adjust the pH values of the solution to neutral. The resulting solution was evaporated under vacuum at 80° C. to remove DMSO. The residue was dissolved in NaOH solution (200 mL; 1 mol/L) containing 6% methanol (9.6 ml) and hydrolyzed for 24 h at room temperature. The solvent was removed by vacuum to obtain BEE-COOH. BEE-COOH (4 g) was dissolved in 20 mL dry THF. Phosphorus tribromide (0.9 mL) was dissolved in 10 mL dry THF and added dropwise. The reaction took 5 h under argon gas at reflux conditions. The resulting suspension was filtered and the clear solution was evaporated under vacuum to remove the solvent THF. The residue was dried under vacuum at 80° C. for 48 h and obtained BEE-COBr.

Scheme 1

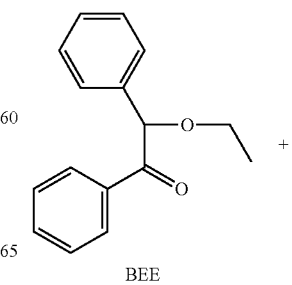

-continued

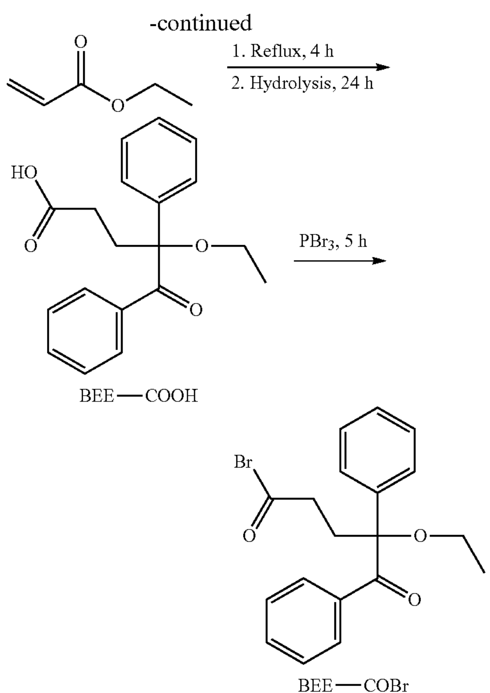

Grafting of PSSA and Poly(Vinyl Imidazolium Chloride)

The modification procedures for grafting poly(styrene sulfonated acid) (PSSA) and poly(vinylimidazolium chloride) ionic liquid on a membrane are presented in FIG. 2. First, amino group ended SAM layer was formed on the membrane surface and then this SAM layer was used to immobilize ATRP and UV initiators, followed by the ATRP of sodium 4-styrenesulfonate. The UV grafting of N-vinyl imidazole (VI) was subsequently carried out. After that, the poly(vinyl imidazole) was treated with HCl.

For immobilizing ATRP and UV initiators on the membrane surface, a SAM layer of 3-aminopropyl-triethoxysilane was first formed. The membrane was immersed in a 30 mL 1:1 (v:v) mixture of ethanol and Milli-Q water containing 120 μL 3-aminopropyl-triethoxysilane and 154 glacial acetic acid. After 1 h, the membrane was removed from the bath. The silane layer was then cured by placing the membrane in an oven at 115° C. for 30 min. Finally, the membrane was ultrasonicated in ethanol for 1 min, further dried in vacuum oven at 40° C.

The amino group ended SAM layer can react with ATRP and UV initiators. The membrane comprising the SAM layer was placed in 10 mL dry THF containing, triethylamine (200 μL), 200 μL 2-bromo-2-methylpropionyl bromide (ATRP initiator) and 0.6 g BEE-COBr (UV initiator). The vessel was then sealed. After reaction for 8 h at 0° C., the membrane was taken out and rinsed with THF and water, and then washed in water overnight.

Subsequently ATRP of sodium 4-styrenesulfonate (NaStS) was carried out. The initiator immobilized membrane sample was placed in a flask, the flask was evacuated and backfilled with argon three times. NaStS was dissolved in 40 mL water/methanol mixture solution (1:1, v/v) and then purged with nitrogen for 30 min. Thereafter, bpy ligand (148 mg) and copper(I) chloride (47 mg) were added to the solution under strong stirring and argon stream. After nitrogen purging for another 10 min, reaction solution was cannulated into the flask and the reaction mixture was incubated at room temperature for predetermined reaction time. The membrane was quickly removed from the flask and immersed in 50 mL 1:1(v/v) methanol/water solution of 250 mg copper(II) chloride and 625 μL N,N,N',N",N"-pentamethyl diethylenetriamine. A water/methanol/ethanol washing sequence was then used to clean the functionalized membrane. The membrane was dried in vacuum oven at 40° C. overnight.

Following drying, PVI was tethered to glass slide surface by UV-induced graft polymerization. The membrane was fixed between two filter papers (Whatman, No. 1) and immersed into 10 mL of N-vinyl imidazole (VI) monomer solution (100 g/L in water) in a Petri dish. The monomer solution was degassed with argon for at least 30 min before use. Then, UV irradiation was administered in a UV reaction box for 15 min. After washing with water, the membrane was dried under vacuum. The poly(vinylimidazole) on the membrane surface was ionized by stay in 12 N HCl solution for 24 h.

Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A porous catalytic membrane comprising:

a surface functionalized with cellulose solubilization functionalities and acid functionalities for the catalytic hydrolysis of cellulose, wherein the cellulose solubilization functionalities are pendant along a polymer chain attached to the surface and comprise one or more imidazolium salts, wherein the functionalized surface is a first side of the porous membrane for receiving cellulose feedstock, the porous membrane having a pore size sufficient to pass glucose molecules, reducing sugar molecules, oligosaccharides or mixtures thereof.

2. The catalytic membrane of claim 1, wherein the one or more imidazolium salts is of the formula:

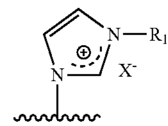

wherein ∿∿ is a point of attachment to the polymer chain, $X^-$ is a counterion and $R_1$ is selected from the group consisting of hydrogen, alkyl, alkyl-sulfonic acid, alkyl-carboxylic acid and alkyl-phosphonic acid.

3. The catalytic membrane of claim 1, wherein the one or more imidazolium salts is of the formula:

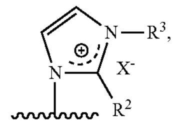

wherein ∿∿ is a point of attachment to the polymer chain, $X^-$ is a counterion and $R^2$ and $R^3$ are independently selected from the group consisting of -hydrogen and -alkyl.

4. The catalytic membrane of claim 1, wherein the acid functionalities comprise sulfonic acid, carboxylic acid or phosphonic acid functionalities or mixtures thereof.

5. The catalytic membrane of claim 1, wherein the acid functionalities are pendant along a cellulose hydrolysis polymer chain attached to the surface of the catalytic membrane.

6. The catalytic membrane of claim 5, wherein the acid functionalities comprise sulfonic acid, carboxylic acid or phosphonic acid functionalities or mixtures thereof.

7. The catalytic membrane of claim 1, wherein the oligosaccharides have a molecular weight less than about 500 g/mol.

8. The catalytic membrane of claim 1, wherein a plurality of pores of the porous membrane are functionalized with acid functionalities for the catalytic hydrolysis of cellulose.

9. The catalytic membrane of claim 1, wherein the acid functionalities are operable for the catalytic hydrolysis of hemicellulose.

* * * * *